United States Patent [19]

Pai et al.

[11] Patent Number: 5,084,480
[45] Date of Patent: Jan. 28, 1992

[54] PENTAMIDINE SALTS USEFUL IN THE TREATMENT OF PNEUMOCYSTIS CARINII PNEUMONIA

[75] Inventors: Sadanand Pai, Burr Ridge; Abu S. Alam, Libertyville; John N. Kapoor, Lake Forest, all of Ill.

[73] Assignee: Fujisawa USA, Inc., Deerfield, Ill.

[21] Appl. No.: 383,243

[22] Filed: Jul. 19, 1989

Related U.S. Application Data

[63] Continuation of Ser. No. 118,284, Nov. 6, 1987, abandoned.

[51] Int. Cl.$^5$ ............................................. A61K 31/205
[52] U.S. Cl. .................................... 514/554; 562/587; 562/589
[58] Field of Search .................. 562/589, 587; 514/554

[56] References Cited

U.S. PATENT DOCUMENTS

| | | |
|---|---|---|
| 2,204,983 | 6/1940 | Ewins et al. |
| 2,277,861 | 3/1942 | Ewins et al. |
| 2,277,862 | 3/1942 | Ewins et al. |
| 2,410,796 | 11/1946 | Newberry et al. |
| 2,424,325 | 7/1947 | Newberry et al. |
| 2,425,223 | 8/1947 | Barber. |
| 2,449,724 | 9/1948 | Short et al. |
| 3,105,853 | 10/1963 | McKay et al. |
| 4,034,010 | 7/1977 | Hamano et al. |
| 4,097,525 | 6/1978 | Kraska et al. ............... 260/501.14 |
| 4,367,231 | 1/1983 | Kornfeld et al. ............. 514/293 |
| 4,501,890 | 2/1985 | Nichols et al. .............. 514/267 |

FOREIGN PATENT DOCUMENTS

729847  2/1953  United Kingdom.

OTHER PUBLICATIONS

Hawley, Gessner G., The Condensed Chemical Dictionary, Von Nostrand Reinhold Co., New York, 10th Ed., p. 143, (1983).

A Chemotherapeutic Comparison of the Trypanocidal Action of Some Aromatic Diamidine Ashley et al., 1942.

PENTAM ™ 300 Package Insert, (no date), p. 1206.

*Primary Examiner*—Bruce Gray
*Attorney, Agent, or Firm*—W. Dennis Drehkoff

[57] ABSTRACT

Salts of pentamidine, formulations containing such salts and the use of such salts of treatment or prophylaxis of pneumocystis carinii. Pentamidine gluconate and lactate has been discovered and found to have high water solubility while providing potentially less toxic alternatives to pentamidine isethionate, especially for aerosolized administration to patients suffering from acquired immunodeficiency syndrome, AIDS, or AIDS related complex, ARC.

11 Claims, No Drawings

PENTAMIDINE SALTS USEFUL IN THE TREATMENT OF PNEUMOCYSTIS CARINII PNEUMONIA

This is a continuation of copending application Ser. No. 118,284, filed on 11/6/87 now abandoned.

FIELD OF THE INVENTION

This application relates, in general, to pentamidine and in particular to new pharmaceutically acceptable salts of pentamidine, to pharmaceutical formulations containing such salts, and to the prophylactic use of such formulations against pneumocystis carinii pneumonia.

BACKGROUND OF THE INVENTION

Pentamidine, in the form of its hydrochloride salt, was first discovered by Ewins et al., as shown in U.S. Pat. No. 2,277,861. Pentamidine and other related compounds were found to have trypanocidal properties. However, pentamidine was initially available only in the form of its hydrochloride salt, which is substantially water insoluble. Because of the therapeutically beneficial results which could be derived from pentamidine, a need arose for water soluble salts of pentamidine. U.S. Pat. No. 2,410,796 to Newberry et al., is directed to such water soluble salts, particularly hydroxy-ethane sulfonic acid salt and hydroxy-propane sulfonic acid salt of pentamidine. The former compound is generally referred to as pentamidine isethionate.

Pentamidine isethionate is presently marketed by LyphoMed, Inc. under the trademark Pentam, for intravenous and intramuscular injection, and is indicated for the treatment of pneumonia due to pneumocystis carinii, the latter ailment typically being referred as "PCP". The importance of pentamidine isethionate has recently dramatically increased due to the marked increase of patients suffering from PCP. The increase in the afflicted patient population is an unfortunate consequence of the increasing presence of the Acquired Immunodeficiency Syndrome ("AIDS"). It is now estimated that approximately 70 percent of all AIDS patients contract PCP. Because of the high incidence of PCP in AIDS patients, pentamidine isethionate has found utility not only in the treatment of PCP, but also for prophylaxis, in preventing the initial onset or recurrence of PCP, especially in AIDS patients.

An unfortunate side effect of pentamidine isethionate is its toxicity. Some fatalities have been attributed to severe hypotension, hypoglycemia, and cardiac arrhythmias in patients treated with pentamidine isethionate, through both intramuscular and intravenous routes. Because of the concern over the potential toxicity of pentamidine isethionate, a need has arisen for a replacement for pentamidine isethionate which may minimize the potential undesirable side effects associated with the use of the drug.

SUMMARY OF THE INVENTION

Several new salts of pentamidine have now been discovered. It is believed that the toxicity of such salts may be appreciably lesser than that of pentamidine isethionate.

Especially surprising embodiments of the present invention are the salts of pentamidine with lactic acid or gluconic acid. The lactic acid and gluconic acid salts of pentamidine have extremely high water solubility, greater than 100 mg/mL, in water. Further, as lactic acid and gluconic acid are both naturally occurring in the human body, it is believed that the use of such acids as the counter-anion will be much more physiologically acceptable than the presently used 2-hydroxyethyl sulfonic acid which is not naturally occurring in the human body. It is extremely surprising, therefore, to discover not only two new salts of pentamidine having high water solubility, but also to find that such salts can be made, in which the anion is naturally present in the human body.

The other pentamidine salts of the present invention are formed with acetic acid, tartaric acid, citric acid, phosphoric acid, boric acid, nitric acid, and sulfuric acid. These salts are characterized by their substantial insolubility in water. Because of their water insolubility they may find application in organic based vehicles or in liposomes in which the water insoluble salts become associated with the hydrophobic portion of the lipid bilayer. In contrast, the water soluble salts of the present invention, pentamidine gluconate and pentamidine lactate, may find application in the form of liposomal formulations in which the gluconate or lactate salt, due to its high water solubility, becomes associated with the hydrophilic inner-portion of the lipid vesicles.

Generally, the present invention also provides pharmaceutical formulations comprising the aforementioned pentamidine salts in physiologically acceptable carriers. Also, the present invention provides pentamidine salts which have been lyophilized and which may be reconstituted to form pharmaceutically acceptable formulations for administration, by intravenous or intramuscular injection.

Further, the present invention provides the aforementioned pentamidine salts as formulations for administration as aerosolized droplets for inhalation.

DETAILED DESCRIPTION OF THE PREFERRED EMBODIMENTS

As indicated, the present invention provides several previously unknown salts of pentamidine. In particular, the salts of the present invention include pentamidine gluconate, pentamidine lactate, pentamidine acetate, pentamidine tartarate, pentamidine citrate, pentamidine phosphate, pentamidine borate, pentamidine nitrate, and pentamidine sulfate.

The present invention provides both water soluble pentamidine salts as well as water insoluble pentamidine salts. As used in the present specification, the term "water soluble" is meant to define any composition which is soluble in water in an amount of about 50 mg/mL, or greater. Also, as used in the present specification, the term "water insoluble" is meant to define any composition which has a solubility in water of less than about 20 mg/mL. For certain applications, water soluble salts may be desirable whereas for other applications water insoluble salts may likewise be desirable. Accordingly, the present invention provides both.

As indicated, surprisingly it has been found that pentamidine gluconate and pentamidine lactate are water soluble and in fact possess an extremely high degree of water solubility, greater than 100 mg/mL. This finding is particularly important in view of the fact that the acids from which the salts are derived, lactic acid and gluconic acid, both occur in small quantities in almost every organ of the human body, as well as in blood and other body fluids. Therefore, a salt of pentamidine formed from gluconic acid or lactic acid should be highly compatible with body fluids, thus increasing the efficacy of the drug, while at the same time reducing its toxicity.

The salts of the present invention are prepared, in general, by reacting the free pentamidine base with slightly in excess of two equivalents of the desired acid, in aqueous solution. After the reaction is complete, the salts are crystallized from the aqueous solution by the addition of an appropriate amount of organic solvent.

In particular, salts of the present invention may be prepared through a relatively straight forward synthesis. Thus, in accordance with one process, pentamidine isethionate, such as that manufactured and sold under the trademark PENTAM by LyphoMed, Inc. may be dissolved in distilled water and then reacted with sufficient ammonium hydroxide to adjust the pH of the solution to about 11. Upon refrigerated storage, crystals of pentamidine free base are generated which can be filtered, washed with distilled water, and dried in a vacuum chamber. The free base may then be contacted with the desired free acid, in distilled water, with stirring. In the case of the water soluble salts, pentamidine lactate and pentamidine gluconate, an organic solvent such as acetone may be added to the aqueous solution until it becomes cloudy, followed by refrigeration which causes crystallization of the pentamidine salt which may then be filtered, washed with organic solvent and dried. The other pentamidine salts may be prepared in a similar fashion, except that the aqueous solution of the acid and free base, after mixing, requires either slight warming or heating to effect salt formation.

As an alternate process, the desired salts may be synthesized from key intermediates. Thus, for example, the 4:4'-di-iminoether of diphenoxypentane may be reacted with the corresponding ammonium salt, such as ammonium lactate or ammonium gluconate. The desired pentamidine salt may then be recrystallized from the appropriate solvent, filtered and dried.

The present invention provides pharmaceutical compositions suitable for intraveneous or intramuscular injection. The pharmaceutical compositions comprise a pentamidine salt selected from the group consisting of pentamidine gluconate, pentamidine lactate, pentamidine acetate, pentamidine tartarate, pentamidine citrate, pentamidine phosphate, pentamidine borate, pentamidine nitrate, and pentamidine sulfate. The desired pentamidine salt may be placed in any pharmaceutically acceptable carrier. If a solution is desired, water is the carrier of choice with respect to pentamidine gluconate and pentamidine lactate. With respect to the remaining pentamidine salts, an organic vehicle, such as glycerol, propyleneglycol, polyethyleneglycol, or mixtures thereof may be suitable. In the latter instance, the organic vehicle may contain a substantial amount of water.

Pentamidine gluconate and pentamidine lactate may both be readily formulated into a pharmaceutical composition. For example, the salt may first be dissolved in water to make a solution generally comprising from about 50 to about 100 mg of pentamidine per mL of water. The solution may then be sterilized in any suitable manner, preferably by filtration through a 0.22 micron filter. Subsequent to sterilization, the solution may be filled into appropriate receptacles, such as depyrogenated glass vials. Of course, the filling should be done by an aseptic method. Sterilized closures may then be placed on the vials and, if desired, the vial contents may be lyophilized.

In addition to the pentamidine salt, the pharmaceutical compositions may contain other additives, such as pH adjusting additives. In particular, useful pH adjusting agents include acids or bases or buffers, such as sodium lactate, sodium acetate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, the pharmaceutical compositions of the present invention may be lyophilized using techniques well known in the art.

In accordance with the present invention, other pharmaceutical compositions may be prepared from the water insoluble pentamidine salts, such as aqueous based emulsions. In such an instance, the composition will contain a sufficient amount of a pharmaceutically acceptable emulsifying agent to emulsify the desired amount of pentamidine salt. Particularly useful emulsifying agents include phosphatidyl cholines, and lecithin.

Further, the present invention provides liposomal formulations of pentamidine salts selected from the group consisting of pentamidine gluconate, pentamidine lactate, pentamidine acetate, pentamidine tartarate, pentamidine citrate, pentamidine hydrochloride, pentamidine phosphate, pentamidine borate, pentamidine nitrate, pentamidine sulfate, and pentamidine isethionate. The technology for forming liposomal suspensions is well known in the art. When the pentamidine salt of interest is an aqueous soluble salt, pentamidine gluconate, pentamidine lactate or pentamidine isethionate, using conventional liposome technology, the same may be incorporated into lipid vesicles. In such an instance, due to the water solubility of the salt, the pentamidine salt will be substantially entrained within the hydrophilic center or core of the liposomes. The lipid layer employed may be of any conventional composition and may either contain cholesterol or may be cholesterol-free. When the pentamidine salt of interest is a water insoluble pentamidine salt, again employing conventional liposome formation technology, the salt may be substantially entrained within the hydrophobic lipid bilayer which forms the structure of the liposomes. In either instance, the liposomes which are produced may be reduced in size, as through the use of standard sonication and homogenization techniques.

Of course, the liposomal formulations containing the pentamidine salts of the present invention may be lyophilized to produce a lyophilizate which may be reconstituted with a pharmaceutically acceptable carrier, such as water, to regenerate a liposomal suspension.

An especially attractive aspect of the present invention are pharmaceutical formulations which are suitable for administration as an aerosol, by inhalation. These formulations comprise a solution or suspension of the desired pentamidine salt selected from the group consisting of pentamidine gluconate, pentamidine lactate, pentamidine acetate, pentamidine tartarate, pentamidine citrate, pentamidine hydrochloride, pentamidine phosphate, pentamidine borate, pentamidine nitrate, and pentamidine sulfate. The desired formulation is placed in a small chamber and nebulized. Nebulization may be accomplished by compressed air or by ultrasonic energy to form a plurality of liquid droplets comprising the pentamidine salts. The liquid droplets should have a particle size in the range of about 0.5 to about 5 microns. Most preferably, the size of the droplets will be from about 1 to about 2 microns. In this respect, commercial nebulizers are available to achieve this purpose.

Preferably, the pharmaceutical formulation suitable for administration as an aerosol will comprise pentamidine gluconate or pentamidine lactate in a carrier which comprises water. A surfactant may be present which lowers the surface tension of the formulation sufficient to result in the formation of droplets within the desired size range when subjected to nebulization.

It is believed that the pentamidine gluconate and pentamidine lactate when administered via the aerosolized route will result in substantially reduced patient discomfort when compared to aerosolized forms of pentamidine isethionate. This is believed to be true due to the fact that the lactic and gluconic acids from which the salt is derived, should be substantially better tolerated than the isethionate salt, especially considering the fact that the aerosolized route requires the salts in the aerosolized form to be placed into direct contact with the patient's mucous membranes.

One of the especially important aspects of the present invention is the provision of a method for treating pneumocystis carinii pneumonia. This method comprises administering to a patient suffering from pneumocystis carinii pneumonia, a therapeutically effective amount of a pentamidine salt selected from the group consisting of pentamidine gluconate, pentamidine lactate, pentamidine acetate, pentamidine tartarate, pentamidine citrate, pentamidine phosphate, pentamidine borate, pentamidine nitrate, and pentamidine sulfate. In accordance with the method, the pentamidine salt may be administered intramuscularly or intravenously as a solution, suspension, or emulsion. Alternatively, the pentamidine salt may also be administered intravenously or intramuscularly as a liposomal suspension. As discussed previously, an especially preferred route of administration in the treatment of pneumocystis carinii pneumonia, is by inhalation in the form of a plurality of droplets having a particle size from about 0.5 to about 5 microns, preferably from about 1 to about 2 microns.

Besides providing a method for treating pneumocystis carinii pneumonia, the present invention also provides a method for prophylaxis against pneumocystis carinii pneumonia in an immunocompromised patient, such as one suffering from AIDS, who has had at least one episode of pneumocystis carinii pneumonia, but who at the time of treatment is not exhibiting signs of pneumocystis carinii pneumonia. As pneumocystis carinii pneumonia is an especially potentially devastating disease for immunocompromised patients, it is preferable to avoid the onset of pneumocystis carinii pneumonia, as compared to treating the disease after it has become symptomatic. Accordingly, the present invention provides a method for the prophylaxis against pneumocystis carinii pneumonia comprising administering to the patient a prophylactically effective amount of a pentamidine salt selected from the group consisting of pentamidine gluconate, pentamidine lactate, pentamidine acetate, pentamidine tartarate, pentamidine citrate, pentamidine phosphate, pentamidine borate, pentamidine nitrate, and pentamidine sulfate. The forms for administration of the pentamidine salt in accordance with this method may be the same as utilized for the purpose of actually treating a patient suffering from pneumocystis carinii pneumonia.

An additional useful aspect of the present invention is a method for prophylaxis against even an initial episode of pneumocystis carinii pneumonia in an immunocompromised patient who has never experienced an episode of pneumocystis carinii pneumonia. In this respect, a patient who has been diagnosed as being immunocompromised, such as one suffering from AIDS or ARC (AIDS related complex), even before the onset of an initial episode pneumocystis carinii pneumonia, may avoid the need to suffer from the infection by having administered a prophylactically effective amount of a pentamidine salt. Again, the useful salts are those indicated above with respect to the treatment of pneumocystis carinii pneumonia and the pentamidine salt may be administered in the same fashion as in the treatment of patients suffering from pneumocystis carinii pneumonia.

In yet another aspect of the present invention, there is provided an injectable, stable, sterile composition comprising a pentamidine salt selected from the group consisting of pentamidine gluconate, pentamidine lactate, pentamidine acetate, pentamidine tartarate, pentamidine citrate, pentamidine phosphate, pentamidine borate, pentamidine nitrate, and pentamidine sulfate, in a unit dosage form in a sealed container. The pentamidine salt is provided in the form of a lyopholizate which is capable of being reconstituted with a suitable pharmaceutically acceptable carrier to form a liquid composition suitable for injection thereof into man. The unit dosage form typically comprises from about 10 mg to about 10 grams of the pentamidine salt. When the pentamidine salt is substantially water insoluble, a sufficient amount of emulsifying agent which is physiologically acceptable may be employed in sufficient quantity to emulsify the pentamidine salt in an aqueous carrier. One such useful emulsifying agent is phosphatidyl choline.

The present invention will be further illustrated by the following non-limiting examples.

EXAMPLE 1

This example demonstrates the preparation of pentamidine free base.

In a one liter beaker, 50 grams of pentamidine isethionate was dissolved in 500 mL distilled water. Ammonium hydroxide was added to the concentrated solution of pentamidine isethionate, with constant stirring, until the pH of the solution was about 11. The solution was then refrigerated overnight and the next day crystals of pentamidine free base were filtered, washed with distilled water, and dried in a vacuum chamber. The yield of free base was 26.2 grams.

EXAMPLE 2

This example demonstrates the preparation of pentamidine lactate. In a 500 mL beaker, 2.5 grams of lactic acid (85 percent) was mixed with 50 mL distilled water and the solution was stirred with a magnetic stirrer. Four grams of pentamidine free base from Example 1 were added to the stirring solution, and the stirring continued until all of the free base was dissolved to form a clear solution. Acetone was then added to the solution in gradual amounts until the solution became cloudy. The beaker was then covered with aluminum foil and refrigerated overnight. Pentamidine lactate crystals were formed and were filtered, washed with acetone, and dried in vacuum. The yield was 5.21 grams.

EXAMPLE 3

In accordance with the process described in Example 2, other pentamidine salts as listed in Table 1 were prepared in a similar fashion, with the exception that the aqueous solution of the acid and pentamidine free base after mixing required either slight warming or heating to affect the salt solution.

TABLE I
Pentamidine Salts

| Compound | Formula | Solubility in $H_2O$ mg/mL |
|---|---|---|
| Pentamidine Gluconate | $C_{19}H_{24}O_2N_4 2C_6H_{12}O_7$ | 114.8 |
| Pentamidine Lactate | $C_{19}H_{24}O_2N_4 2C_3H_6O_3$ | 100.3 |
| Pentamidine Acetate | $C_{19}H_{24}O_2N_4 2C_2H_4O_2$ | 17.0 |
| Pentamidine Tartarate | $C_{19}H_{24}O_2N_4 2C_4H_6O_6$ | 3.4 |
| Pentamidine Citrate | $C_{19}H_{24}O_2N_4 2C_6H_8O_7$ | 0.6 |
| Pentamidine Hydrochloride | $C_{19}H_{24}O_2N_4 2HCl$ | 14.5 |
| Pentamidine Phosphate | $C_{19}H_{24}O_2N_4 2H_3PO_4$ | 16.8 |
| Pentamidine Borate | $C_{19}H_{24}O_2N_4 2H_3BO_3$ | 6.9 |
| Pentamidine Nitrate | $C_{19}H_{24}O_2N_4 2HNO_3$ | 1.8 |
| Pentamidine Sulfate | $C_{19}H_{24}O_2N_4 2H_2SO_4$ | 1.4 |

What we claim is:

1. A salt of pentamidine with an acid selected from the group consisting of gluconic acid and lactic acid.

2. The salt of claim 1 wherein the acid is gluconic acid.

3. The salt of claim 1 wherein the acid is lactic acid.

4. Pharmaceutical composition suitable for intravenous or intramuscular injection comprising a pentamidine salt selected from the group consisting of pentamidine gluconate and pentamidine lactate and a pharmaceutically acceptable carrier.

5. The composition of claim 4 wherein the carrier comprises water.

6. The composition of claim 5 also comprising a buffering agent.

7. The composition of claim 5 which has been lyophilized.

8. The composition of claim 7 wherein the composition also comprises an agent for adjusting the tonicity of the composition.

9. A pharmaceutical formulation suitable for administration as an aerosol, by inhalation, comprising a solution or suspension of a pentamidine salt selected from the group consisting of pentamidine gluconate and pentamidine lactate and a physiologically acceptable carrier; the solution or suspension being capable of being nebulized to form a plurality of liquid droplets comprising the pentamidine salt and having a particle size in the range of about 0.5 to about 5 microns.

10. The formulation of claim 9 wherein the carrier comprises water.

11. The formulation of claim 9 wherein the solution upon being nebulized forms a plurality of liquid droplets having a particle size from about 1 to about 2 microns.

* * * * *